United States Patent [19]

Neckers et al.

[11] Patent Number: 5,606,171

[45] Date of Patent: Feb. 25, 1997

[54] METHOD FOR DETERMINING THICKNESS, DEGREE OF CURE AND OTHER PROPERTIES OF A POLYMERIC COATING OR FILM

[75] Inventors: Douglas C. Neckers, Perrysburg; Jian C. Song, Bowling Green; Afranio Torres-Filho, Bowling Green; Wolter F. Jager, Bowling Green; Zhijun J. Wang, Bowling Green, all of Ohio

[73] Assignee: Spectra Group Limited, Inc., Maumee, Ohio

[21] Appl. No.: 461,644

[22] Filed: Jun. 5, 1995

Related U.S. Application Data

[63] Continuation-in-part of Ser. No. 238,459, May 5, 1994.

[51] Int. Cl.$^6$ ................................................ G01N 21/64
[52] U.S. Cl. .................. 250/459.1; 250/302; 250/458.1; 250/461.1
[58] Field of Search ............................ 250/302, 461.1, 250/459.1, 458.1

[56] References Cited

U.S. PATENT DOCUMENTS

| | | | |
|---|---|---|---|
| 4,250,382 | 2/1981 | Libby | 250/302 |
| 4,651,011 | 3/1987 | Ors et al. | 250/459.1 |
| 4,922,113 | 5/1990 | Melancon | 250/461.1 |
| 5,037,763 | 8/1991 | Petisce | 250/302 |
| 5,158,720 | 10/1992 | Levy | 250/458.1 |
| 5,453,625 | 9/1995 | Lawson et al. | 250/302 |
| 5,464,986 | 11/1995 | Boettcher et al. | 250/302 |

FOREIGN PATENT DOCUMENTS

| | | | |
|---|---|---|---|
| 530095 | 3/1993 | European Pat. Off. | |
| 145163 | 11/1979 | Japan | 250/458.1 |
| 1311932 | 3/1973 | United Kingdom | 250/461.1 |

OTHER PUBLICATIONS

Zhang et al., "Real–Time Monitoring . . . Systems", *J. Imaging Sc. and Tech.* 36, No. 4 (1992).

Paczkowski et al., "New Fluorescence Probes for . . . Polymerization" *J. Polymer Sc. Part A: Polymer Chem.*, 31, 841–846 (1993).

Paczkowski et al., "Following Polymerization Kinetics . . . Methodology", *Macromolecules*, 25 (1992).

Paczkoski et al., "Developing Fluorescence Probe Tech . . . Polyolacrylates," *Chemtracts—Macromolecular Chem.*, 3 75–94 (1992).

Loutfy, "High–Conversion Polymerization . . . Methacrylate", *Macromolecules*, 14, 270–275, (1981).

*Primary Examiner*—Carolyn E. Fields
*Attorney, Agent, or Firm*—Thompson Hine & Flory LLP

[57] ABSTRACT

A method for monitoring a property of a polymeric mass such as a coating or film comprising the steps of adding a fluorescence probe compound capable of fluorescing to a polymeric composition which has the ability to undergo changes in microviscosity, the ratio of the intensity of the fluorescence emission of said compound at two wavelengths changing in response to said changes in said microviscosity of said composition; curing said composition; causing said compound to fluoresce; measuring the fluorescence of said compound; calculating the ratio of the intensities of fluorescence emission of said compound at two or more wavelengths; relating said ratio to the monitored property of said composition.

15 Claims, 5 Drawing Sheets

METHOD FOR DETERMINING THICKNESS, DEGREE OF CURE AND OTHER PROPERTIES OF A POLYMERIC COATING OR FILM

This is a continuation-in-part of application Ser. No. 08/238,459, filed May 5, 1994.

BACKGROUND OF THE INVENTION

The present invention relates to a method for monitoring thickness, degree of cure, and other properties of a coating or film using fluorescence methodologies.

Fluorescence spectroscopy has received considerable interest as an analytical tool due to its high sensitivity, selectivity and non-destructive characteristics. In addition, remote sensing is readily available using fluorescence methods through the use of fiber-optic cables to transmit optical signals to and from the analytical site in real time. Fluorescence spectroscopy has proven to be an extremely useful analytical tool in polymer chemistry. The technique has provided valuable information on the mechanisms and kinetics of polymerization, curing and crosslinking as well as oxidation, degradation and stabilization. The technique of fluorescence spectroscopy has been particularly useful in elucidating polymer properties such as their macro or supermolecular structure, molecular weight, viscosity and permeability.

Fluorescence probes as hereafter defined, have been used to study polymerization kinetics. For example, Paczkowski and Neckers, "Following Polymerization Kinetics of Multifunctional Acrylates in Real Time by Fluorescence Probe Methodology, *Macromolecules*, 25, 548–553 (1992) discusses the use of fluorescing probes such as dansylamide to follow the kinetics of polymerization and post-irradiation processes of multifunctional acrylates in real time. Other articles describe the use of fluorescence probes in polymerization studies of acrylates such as Paczkowski and Neckers, "Developing Fluorescence Probe Technology for Monitoring the Photochemical Polymerization of Polyolacrylates," *Chemtracts-Molecular Chemistry*, vol. 3, 75–94 (1992); Paczkowski and Neckers, "New Fluorescence Probes for Monitoring the Kinetics of Laser-Initiated Polymerization," *JPS: Part A: Polymer Chemistry*, vol. 31, 841–846 (1993); and Zhang, Kotchetov, Paczkowski and Neckers, "Real Time Monitoring of Polymerization Rates of Polyacrylates by Fluorescence Probes II. Effect of Depth of Polymerization for a Bleaching Photoinitiator System," *The Society for Imaging Science and Technology*, vol. 36, No. 4, 322–327, July/August 1992.

DEFINITION

The term "fluorescence probe" as used herein means a compound, the fluorescence characteristics of which, when added to a fluid solution which undergoes a change in microviscosity sometimes leading to a gel or a solid, are dependent upon the microenvironment of the fluorescing species. In accordance with the present invention, the changes in the fluorescent characteristics are related to changes in chemical, physical, and/or mechanical characteristics of the coating.

The term "cure" as used herein includes any process by which a polymeric mass is hardened including, by way of example, crosslinking, polymerization, and solidification through evaporation of a solvent or through cooling (e.g., a hot melt composition).

SUMMARY OF THE INVENTION

In accordance with the present invention, methods are provided for measuring the properties of an uncured, curing or a cured polymeric mass such as a coating or film using fluorescence methodologies. Properties which can be monitored in accordance with the invention include degree of cure, hardness, abrasion resistance, resistance to strain, tactility, elasticity, molecular orientation, tensile strength, modulus, stress state of solids, wetness and dryness. In one method, fluorescence is induced in a substrate such that the thickness (or coat weight) of a coating on the substrate can be determined through an application of Beer's law. The reduction in intensity due to absorption of substrate fluorescence by the coating is used to monitor the thickness of the coating. In another method, a fluorescence probe is provided in the coating or film and the changes in the fluorescent characteristics of the probe are observed. Using previously prepared calibration curves, these changes can be related to various properties of the coating and particularly to the degree of cure. While the invention is principally applicable to monitoring the properties of coatings and films, those skilled in the art will appreciate that these properties can be measured in a polymeric mass of any geometry or shape provided, of course, that the mass in at least one dimension transmits the fluorescence such that it can be detected. Hence, the invention broadly relates to the use of the disclosed methodologies in monitoring the properties of a polymeric mass of any shape.

Using the foregoing fluorescence based methodologies, methods are provided whereby the properties of a coating can be monitored in an industrial setting. These methods may be used in-line or off-line to enable the coating manufacturer to determine any variance in the coating and to adjust the coating parameters as necessary to correct for the variance. Among the coating parameters that might be adjusted in response to a detected variance are coating application rate, line speed, cure time, drying time, irradiation intensity, dosage, etc.

The present invention also provides an apparatus for monitoring coating or film parameters in-line or near-line which comprises an array of optical fibers located adjacent the coating in a light-tight chamber on a coating manufacturing line which is coupled with a fluorescence detector. A source of monochromatic excitation energy is associated with the array such that fluorescence is induced in the substrate for thickness determination in accordance with the first method or in the coating for determination of other properties in accordance with the second method. By sequentially sampling the fluorescence emission data and comparing the observed fluorescence with calibration data using a data processor or computer, the coating thickness and properties can be monitored on-line or near-line.

In more detail, one manifestation of the invention is a method for measuring the thickness or coat weight of a polymeric coating on a substrate. This method comprises the steps of:

providing a substrate having a nascent (inherent) fluorescence emission or a substrate which has been doped with a fluorescer;

causing a first fluorescence intensity in said substrate at a first predetermined wavelength, measuring said first fluorescence intensity;

applying a coating containing an absorber of said first fluorescence onto said substrate;

causing a second fluorescence intensity at said first predetermined wavelength;

measuring said second fluorescence intensity; and determining the thickness of said coating based upon the ratio of said first and said second fluorescence intensities.

While it is known in the art from Beers law that the thickness of a coating can be determined from the change in intensity of light passing through the coating and, more particularly, from the log of the ratio of intensity I/Io where I is the intensity of light passing through the coating and Io is the intensity of light incident the coating, this property has not been applicable in many coating operations such as in coating containers due to the inability to position a detector on the side of the coating opposite the light source due to the presence of or interference from the coated substrate. However, by using fluorescence emission to measure thickness in accordance with the present invention, a light source in the form of fluorescence emission can be induced on the side of the coating facing on the substrate, and a detector can be positioned adjacent the free surface of the coating (i.e., the coating surface opposite the substrate) to measure the fluorescence intensity from which the thickness of the coating can be determined.

In another manifestation of the invention, fluorescence analysis is used to determine any of a number of coating or film properties such as the degree of cure, hardness, abrasion resistance, resistance to stain, tacticity, elasticity, molecular orientation, tensile strength, viscosity, modulus, stress state, wetness, resistance to smear or smudge, and others by relating the change in the fluorescence of a probe in the coating or film to a change in one or more of these properties. These properties may be measured individually, in combination, or in conjunction with the measurement of the coating thickness as previously described.

The ultimate properties of the polymeric network which constitutes a mass such as a coating or film depend on various factors, such as monomer structure, forms of initiation, reaction conditions and the rate and degree of polymerization. These properties affect the microenvironment of the fluorescence probe and, thus, cause changes in its fluorescence. Probe fluorescence changes accompanying polymerization in photochemical processes, and others, are related both to changes in the microviscosity and the local polarity of the probe induced both by the solid polymers and the resulting polymeric solutions. By measuring the intensity of the fluorescence at two or more wavelengths and calculating the ratio of the intensities ($I_{\lambda a}/I_{\lambda b}$) for different predetermined coating or film-forming conditions such as degree of cure, hardness, tacticity, elasticity, etc., calibration curves can be constructed from which dynamic properties can be determined using fluorescence measurements. For example, by using such techniques as infrared transmission in thin films (FTIR), differential scanning calorimetry and the like, the degree of cure, as indicated by double bond conversion, can be determined. By correlating the measured property with fluorescence intensity ratios at two wavelengths or by recording the entire spectrum, for a given probe in a given coating composition, calibration curves can be established such that in an industrial setting, measurement of the intensity ratios can be used to monitor the degree of cure of the coating or film for on-line or off-line process control. In an analogous manner, calibration curves can be established relating fluorescence intensity ratios to other coating properties. Based upon such calibration data, the foregoing method can be used to monitor coating properties.

One method in accordance with the invention comprises the steps of:

providing a fluorescence probe in a curable polymeric mass such as a coating or film;

causing said fluorescence probe to fluoresce wherein said fluorescence probe emits radiation at a multiplicity of wavelengths of measurable intensities;

calculating the ratio of the intensity of the emitted radiation of the probe at two or more predetermined wavelengths;

determining the monitored property of said mass based upon said ratio. The determination is made by comparing the observed ratios to calibration data in which the ratios are correlated with an external measure of the property. This method can be used in combination with the method for determining the coating thickness if the fluorescence emission of the substrate in the first method is distinct from the fluorescence emission of the probe.

The fluorescence probe technology can be used for on-line as well as off-line analysis in both quality control and processing optimization. An on-line monitoring of the degree of cure or any of the other properties previously mentioned can be achieved by continuously or periodically examining the fluorescence emissions spectra of the probe which was doped into the monomer resin at a low concentration (typically 0.02–0.01 wt. %) before the photocuring process. However, in some cases an off-line analysis is recognized to be more practical and economical. An off-line analysis can be achieved by applying a probe solution to the surface of a coating or film or immersing the coating or film in the solution such that the solution swells the polymer and the probe migrates or diffuses into the polymer coating or film. It has been found that polymer properties can be monitored regardless of whether the probe is pre-mixed with the coating polymer or diffused into the coating. The degree of cure of the polymer coating or film can be determined by measuring the fluorescence emission spectrum of the probe. The degree to which the coating or film is swelled by the probe solution and the probe is absorbed by the coating is inversely proportional to the degree to which it is cured.

Accordingly, another method in accordance with the invention comprises the steps of:

diffusing or impregnating a fluorescence probe into a cured polymeric mass such as a coating or film;

causing said fluorescence probe to fluoresce wherein said fluorescence probe emits radiation at a multiplicity of wavelengths of measurable intensities;

calculating the ratio of the intensity of the emitted radiation of the probe at two or more predetermined wavelengths;

determining the monitored property of said coating or film based upon said ratio.

Various fluorophores can be used as probes. These may be added to the to be cured system (so-called extrinsic probes) or they may be intrinsic to the system. Extrinsic probes may be chosen from various kinds including a fluorescence probe which produces an excimer which has a fluorescence emission distinctly different from the fluorescence emission of the monomer of said fluorescence probe, a molecule which produces a fluorescence which is easily susceptible to quenching, or molecules with multiple fluorescence emissions which depend on molecular conformations in the excited state such as those exhibiting Twisted Intramolecular Charge Transfer (TICT) properties.

An apparatus useful in monitoring the aforementioned coating properties using the fluorimetric methods of the invention is also provided.

DETAILED DESCRIPTION OF THE INVENTION

Figure 1:
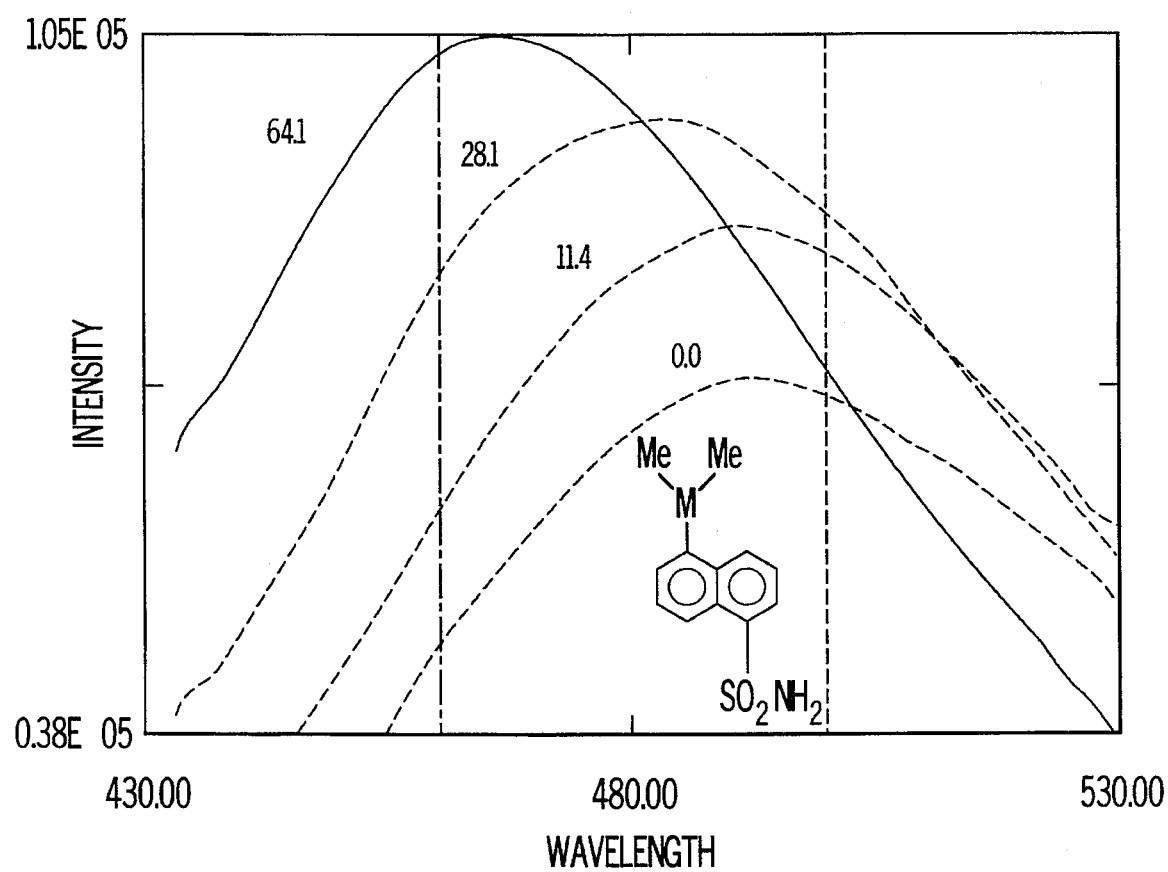
FIG. 1 shows changes in the fluorescence spectra of dansylamide (DA) observed during thermally initiated polymerization of the TMPTA-VP mixture. Numbers above the fluorescence curves indicate the degree of cure.

It has been discovered that the thickness of cured polymeric coatings and films and the degree of cure and other properties of polymeric masses such as coatings and films can be accurately and quickly measured using fluorescence methodology.

Often solid polymers are made in continuous processes from liquids which can be formed, shaped, delivered, or in some other way manipulated in the liquid, and then dried or cured to form the solid, functional product. This process of conversion from a mobile phase to an immobile phase is herein defined as curing. Cured polymeric coatings are used in a variety of applications to provide a durable surface without detracting from the object itself. For example, coatings such as silicone acrylate may be applied to the outside surface of plastic bottles used to contain soft drinks. These bottles are typically made from polyethylene terephthalate (PET) and the silicone acrylate coating, when cured, provides a hard surface having long term durability enabling the bottles to be reused. For environmental reasons, the ability to reuse such plastic bottles is highly desirable.

In order to coat plastic bottles or any substrate, it is necessary, not only to have a method for coating the particular substrate in the mobile uncured phase and curing it to an immobile phase (be that solid, liquid, or gel) but, in many cases, it is also necessary to be able to accurately and quickly determine the thickness of the coating and/or the degree of cure of the coating and other properties as a measure of its efficiency and effectiveness.

In measuring the thickness or coat weight of the coating on a substrate exhibiting nascent or doped fluorescence in accordance with the invention, the uncoated support is irradiated to ascertain the intensity of the fluorescence emission at a given wavelength. The support is then coated with the desired coating and the intensity of the fluorescence emission of the support is remeasured. In all cases the coating or an agent in the coating must absorb the fluorescence of the substrate. Irradiation of the substrate through the coating has the effect of producing a light emission at the interface of the substrate and the coating, which can be used to monitor the thickness of the coating in an industrial setting. The thickness of the coating can then be obtained from a coordinate calibration curve based upon the ratio of the intensities for the uncoated substrates and substrates coated with coatings of known thicknesses.

In measuring the thickness or coat weight of a coating, fluctuations in initial light intensity ($I_O$) and variations in the conversion factor of the detector of the fluorescence emission (D) with intensity can result in significant error. This error can be corrected by incorporating a probe into the coating and monitoring the total fluorescence emission from both the substrate and the probe at two individual wavelengths and then taking the ratio of two signal intensities. The coating thickness can be expressed by the following equation:

$$L = \frac{R - A}{B^*R - C} \qquad \text{Eq. 1}$$

where A, B, and C are known parameters and R is the ratio of the emission intensity at two wavelengths. The unknown parameters can be found by a calibration procedure. If the signal intensity ratios $R_1$, $R_2$, and $R_3$, of three individual samples with known thicknesses $L_1$, $L_2$, and $L_3$ are obtained experimentally, the parameters A, B and C can be calculated. Once the parameters are known, the thickness of the coating layer can be determined using the foregoing equation. The method is illustrated in Example 13.

The method of the present invention is useful in measuring coating thicknesses up to about 1 cm. The upper limit will vary depending upon the extent to which the coating absorbs the excitation radiation. There is no lower limit on the thickness of the coating.

Any of a variety of substrates may be coated and the coating thickness monitored in accordance with the present invention including most natural and synthetic polymeric films such as polyethylene, polypropylene, polystyrene, PET, polyurethanes, epoxies, vinyl such as PVC, polyamides and nylons, polyimides, elastomeric materials and rubbers, composites of materials, fiberglass as well as other materials such as wood, particle board, glass, cement, ceramics, metals, cotton, wool, synthetic fibers, paper, other cellulosics, and virtually any structural material. Most materials, and most polymers exhibit a nascent fluorescence and any substrate having nascent fluorescence can be coated and the thickness of the coating monitored as taught herein by causing fluorescence in that substrate. In the event that the substrate does not exhibit nascent fluorescence, the substrate may be doped with a fluorescer to induce florescence. Fluorescers are commercially available which can be used when necessary in this embodiment of the invention. The amount of the fluorescer used in the substrate can easily be determined such that a fluorescence of measurable intensity is obtained taking into consideration the absorption of the coating of both excitation and emission radiation.

Any of a variety of polymers can be monitored for thickness, degree of cure and other properties in accordance with the teachings of the present invention provided that they transmit a sufficient amount of the excitation energy to induce fluorescence in the substrate in the case of thickness measurement and in the coating itself in the case of the determination of other properties. Examples of polymers include polymerizable and heat cured or dried polymers. Specific examples include any curable (e.g., radiation curable and thermally curable) acrylate such as silicon acrylates, urethane acrylates, epoxy acrylates, polyester acrylates such as trimethylolpropane triacrylate (TMPTA), urethane acrylate, ethoxylated trimethylolpropane triacrylate, 1,1,1-trimethylolpropane triacrylate, dipentaerythritol pentaacrylate, pentaerythritol triacrylate, 1,1,1-trimethylolpropane trimethacrylate, 1-vinyl-2-pyrrolidinone, and mixtures thereof as well as vinyl compounds such as styrene, PVC, and vinyl ethers and unsaturated polyesters. Also included are cycloaliphatic epoxides, aryl, aliphatic or aromatic epoxides such as bisphenol-A epoxide and diglycidyl ether of butane (DGEB) materials used for liquid crystals, holograms and the like.

In order to determine the thickness of a coating, the coating must absorb the fluorescence emission produced in the substrate. While almost all coating compositions will absorb the fluorescence to some degree, in many cases it may be desirable to place an absorber in the coating for this purpose. Any compound which partially absorbs the fluorescence would be potentially useful. Complete absorption would preclude any thickness measurement. Those skilled in the art familiar with the application of Beer's law will understand the nature and amount of absorber that may be used. The fluorescence probes, described herein are generally also useful as absorbers in the measurement of coating thickness. Hence, they provide a means to measure both thickness and other coating properties such as the degree of cure.

Among the myriad of industrial applications in which fluorescence methodologies of the present invention are useful in monitoring coating properties such as thickness and/or degree of cure, several are particularly notable: coating plastic beverage containers with a scratch-resistant finish, as previously mentioned, optical fiber coatings, coating floor tiles and flooring with an abrasion-resistant (no-wax) finish such as an acrylic or polyurethane-acrylates finish, coating papers and films with release films or finishes to provide release sheets useful in the tape and label industries, and acrylate coating of fiber glass.

In measuring the degree of cure of a polymeric mass such as a coating or film material, a fluorescence probe is incorporated into a curable polymeric composition. The fluorescence probe is generally added to the coating material in the amount of about 0.001 to 0.1% by weight of the coating material. This methodology can also be used to monitor the properties of multiple coatings on one substrate.

Figure 5:
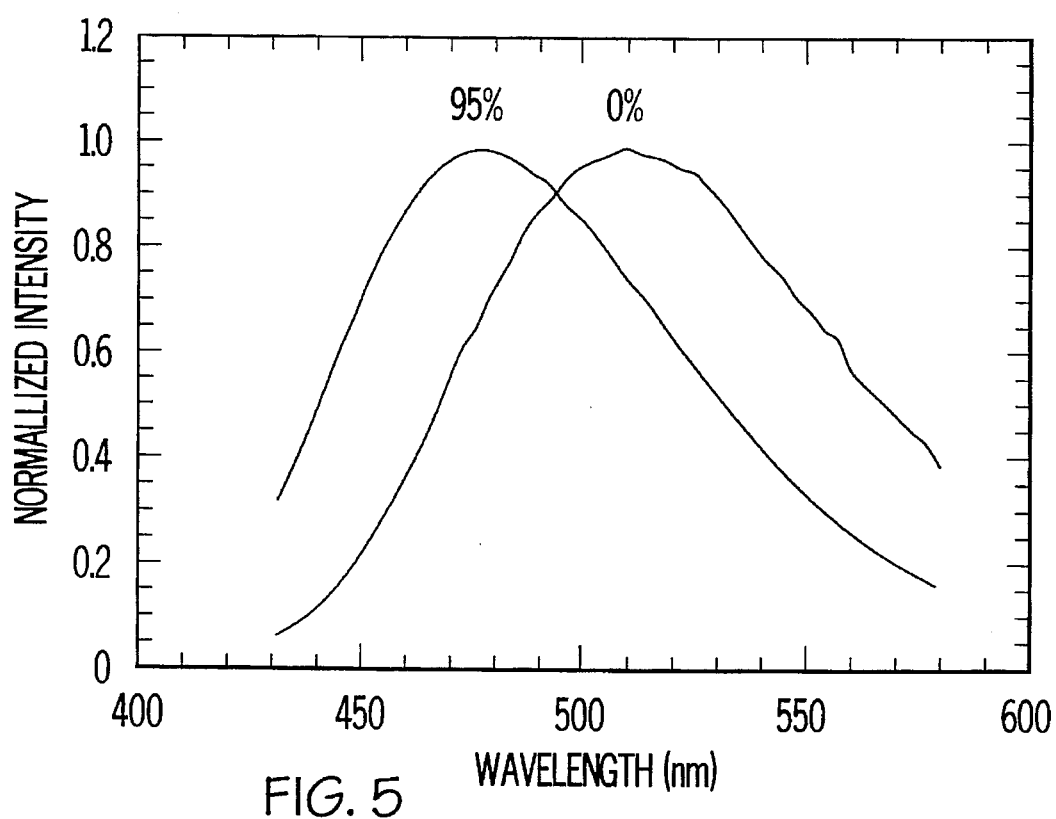
FIG. 5 illustrates the shift in the emission spectrum of 1,5-DASB in a urethane acrylate mixture as a function of degree of cure.

In order to effectively utilize the fluorescence information obtained, the fluorescence probe should absorb light at one wavelength and emit light at a significantly different wavelength to prevent interference. In addition, in monitoring cure or other properties of the mass or coating, the probe must experience a fluorescence shift as a result of chemical and associated physical changes in the mass or coating. Preferably, the probe exhibits a multiplicity of emissions with a large Stokes shift. These emissions exhibit both a wavelength change and an intensity change. One example of a useful spectral shift is shown in FIG. 5 where the emission spectra of the probe 1,5-DASB are provided for a cured and uncured urethane acrylate composition (Example 8).

The fluorescent shift can be the product of a number of different mechanisms. Certain fluorescence probes form intermolecular excimers which are excited dimers thought to be formed by a diffusion—controlled reaction between a molecule in its excited state and another molecule in the ground state. $A^*+A \rightarrow A+A+h\nu$. Such excimers have a different emission spectrum than the monomer, the spectrum is shifted to the shorter wavelengths for the monomeric emitter and to longer wavelength for the excimer. Excimer emission has been shown to be a function of coating viscosity. See Paczkowski and Neckers, supra.

Other fluorescence probes are capable of emitting radiation from different conformations, e.g., from twisted intramolecular charge transfer (TICT) states. The shorter wavelength is thought to be due to a coplanar excited state conformation and the longer wavelength from an excited molecule with a perpendicular conformation. This technique is based upon the difference in fluorescence intensity from the parallel and perpendicular conformations of the excited state of the complex and is based on the dependence of the relative population of each conformation on the microviscosity of the system. As the curing reaction proceeds, the steady state fluorescence emission spectra of the probes have been found to exhibit hypsochromic spectral shifts due to the increase in matrix microviscosity. A linear correlation between the fluorescence intensity ratio ($R=Ipar/Iper$) where Ipar and Iper correspond to the emission intensity values of the parallel and perpendicular conformations of the excited state respectively) and the extent of polymerization, measured by transmission FTIR spectrometry, has been obtained for different types of acrylated polymers cured with UV or visible (VIS) initiators.

The fluorescence probes useful in the invention include dansylamide, 1-(N,N-dimethylamino)-5-n-butylsulfonamido-naphthalene (1,5-DASB), 2-(N,N-dimethylamino)-5-n-butyl-sulfonamide-naphthalene (2,5-DASB), 2-N,N-dimethylamino-6-propanoylnaphthalene (PRODAN), 4-(N,N-dimethylamino) benzonitrile, (DMABN), ethyl 4-(N,N-dimethylamino benzoate, 2-([4-(N,N-dimethylamino) benzoyl]oxy) ethyl methacrylate, butyl 4-(N-piperidino) benzoate, butyl 4-(N-morpholino) benzoate, butyl 4-(N,N-dimethylamino) benzoate, n-butyl 2-dimethylamino-5-naphthalene sulfonate, N-(4'-cyanophenyl)-carbazole, N-(4'-butyl benzoate)carbazole, N-(1'-naphthyl)-carbazole, 9,9'-dianthryl, 4-dimethyl amino-4'nitrostilbene, ethyl-4-dimethylaminobenzoate, 2-dimethylaminonaphthalen-6-sulfonyl-N-butylamide, 6-p-toluidinylnapthalene-2-sulfonyl-N-butylamide, 6-(N-methylanilino)naphthalene-2-sulfonyl-N-butylamide, 5-dimethylaminonaphthalen-1-sulfonyl azidridine, and all of the compounds labeled 15–56 in the paper by W. A. Rettig (Angew. Chem. Int. Ed. English, 25 (1986) page 976) are included. Preferably the fluorescence probes are dansylamide (DA) and (1,5-DASB) and most preferably the fluorescence probe is (1,5-DASB). Fluorescence probes which exhibit TICT include 4-(N,N-dimethylamino)benzonitriles (DMABN) and 4-(N,N-dimethylamino)benzoates (DMB) among others.

The following methods can be used to measure the degree of cure of two coatings. Commercially this methodology can be used to monitor the degree of cure of the primary and secondary coating on an optical fiber. In accordance with one embodiment of the invention, a first fluorescent probe (probe 1) is added to the primary coating, i.e., the first coating applied to the substrate and a second probe (probe 2) is added to the secondary coating. If probe 2 absorbs at wavelengths at which probe 1 is transparent, for example, if probe 2 absorbs at longer wavelengths than probe 1, probe 2 can be excited at a wavelength (the excitation wavelength of probe 2) at which probe 1 is not excited. In this manner, the degree of cure in the secondary coating can be determined without interference from probe 1 and the primary coating. The degree of cure of the primary coating can be determined prior to laying down the second coating by exciting probe 1 at its excitation wavelength, measuring the intensities of the emission of probe 1 at two wavelengths and calculating the ratio of the intensities at the two emission wavelengths and relating this to the degree of cure of the primary coating as previously described herein. Similarly, the degree of cure of the secondary coating can be determined by exciting probe 2 at its excitation wavelength and measuring the emission intensities of probe 2 at two wavelengths, calculating the ratio of the emission intensities and relating the ratio to the degree of cure as discussed herein.

In another embodiment, probe 1 absorbs and emits at longer wavelengths than probe 2. At short wavelengths, the extinction coefficient of probe 2 is considerably higher than that of probe 1. Thus, at short wavelengths, probe 2 can be excited without significantly exciting probe 1. At longer wavelengths the extinction coefficient of probe 2 is low (e.g., zero) while the extinction coefficient of probe 1 is high. At long wavelengths, probe 1 can be excited without exciting probe 2. This means that probe 1 can be excited specifically at a first wavelength at which probe 2 is not excited and the degree of cure of the primary layer in which probe 1 is present can be determined without interference from probe 2 by ratioing the emission intensities at two wavelengths, as discussed above, and relating the ratio to the degree of cure. Light emitted by probe 1 is not absorbed by probe 2. Probe 2 can be excited at a wavelength at which probe 1 is substantially not excited. If the emission spectrum of probe 2 does not significantly overlap that of probe 1, the degree of cure of the secondary layer in which probe 2 is present, can be determined by ratioing the emission intensities and relating this to the degree of cure as described herein.

In a third embodiment of the invention, the probes can be excited simultaneously. In this embodiment, probe 1 emits at a longer wavelength than probe 2 but probe 1 and probe 2 have comparable extinction coefficient at the excitation wavelength. The emission of probe 1 is not absorbed by probe 2. The radiation at that excitation wavelength excites both probe 1 and probe 2. If the overlap of the emission spectra of both probes is negligible, ratioing two emission wavelengths for probe 1 can be used to determine the degree of cure of the primary coating and ratioing the intensities of two emission wavelengths for probe 2 can be used to determine the degree of cure of the secondary coating. Due to the fact that the emission spectra of probe 1 and probe 2 do not overlap, the degree of cure of both the primary and the secondary coating can be determined independently and simultaneously.

To add the probe to the coating or film "off-line", i.e., after applying and curing the coating or film, the probe can be dissolved in a solvent and the film can be immersed in the solution of the probe or the solution of probe can be coated on the coating or film such that the solution swells the polymer and the probe diffuses into the coating or film. The selection of the solvent will depend on the probe and the polymer. Acetone and ethyl acetate are two examples. The concentration of the probe can vary. Concentration on the order of 0.02% are useful for many applications. Concentrations of 0.03 to 0.12% are generally useful. To prevent any surface coating of the probe from interfering with the analysis, the coating or film surface is rinsed with the solvent. The coating or film is then allowed to dry and the coating is analyzed in the same manner as if the probe had been directly incorporated into the films. The probe is preferably dissolved in a solvent which swells the coating or film. The method is described in more detail in Example 14.

The present invention also provides apparatus for practicing the foregoing methods. As with the methods, the apparatus may be designed for off-line or on-line use. The apparatus includes a source of excitation energy, an analytical head which will preferably access multiple sites on a coated substrate of any size and shape, and a data processing program so that the monitored coating property may be determined at any point along the substrate by comparison to calibration data. The detected radiation wavelength will vary with the nature of the support or the selection of the probe. Any fluorescent wavelength (200–800 nm) of measurable intensity is useful. The apparatus may be designed to detect selected wavelengths in the emission spectrum or to detect the entire spectrum. The apparatus may optionally include an alarm circuit which is set to generate a signal if the comparison with the calibration data indicates that there is an unacceptable variance in the monitored coating property. Alternatively, the alarm circuit can interface with other controls to adjust any of the coating conditions previously mentioned so as to directly effect a correction of the variance.

Any convenient source of energy which will activate the fluorescence emission may be employed and any means capable of detecting the fluorescence emission can be used in the present invention. Suitable examples of excitation sources include ultraviolet radiation, electron beam radiation, particle beam radiation, visible light, lasers (e.g., an argon laser), etc. Where light is used as the excitation source, the bandwidth of light which may be used may range from about 0.5 to 10 nm. This will depend on how well the excitation and emission wavelengths are separated from one another as well as on various interferences from other components. As the separation in nanometers increases, broader bandwidth monochromatic radiation may be used.

The apparatus may employ a bifurcated optical fiber array wherein one set of fibers provides the excitation energy to the substrate or coating and another associated set of fibers is coupled to a photodetector and detects fluorescence. This array may assume any design configuration necessary to accommodate the substrate being coated. However, the array will likely be housed in a light-tight chamber. In one embodiment a linear array of optical fiber pairs (i.e., one fiber for excitation and the other for detection) may be positioned immediately adjacent the coated substrate for on-line monitoring of the coating.

The apparatus may include other components of a conventional fluorimeter such as an electronic shutter, a monochromator, a photomultiplier tube as the radiation detector, voltage to current converters which interface with the photomultiplier tube or CCD, focusing lenses, interference filters, neutral density filters, etc. An example of a conventional fluorimeter is provided in Paczkowski, supra, Molecules, vol. 25, No. 2, 1992 at page 552.

While the following examples will reference the measurement of degree of cure, those skilled in the art will appreciate that any of the aforesaid properties can be calibrated and measured in an analogous manner. The degree of cure of a coating can be determined by the fluorescence shift exhibited in a cured coating. The degree of cure can be obtained from a coordinate calibration curve as shown in the examples below.

Example 1

Three flat polyethylene terephthalate samples coated with silicone acrylate at various known thicknesses were individually irradiated with radiation of a wavelength of 302 nm using a SPEX Fluorolog II fluorimeter (Xenon source) and a SPEX 1608 0.22 m monochromator. The nascent fluorescence of the substrate was activated by the radiation and the intensity of the nascent fluorescence emission through the cured coating was measured at a wavelength of 380 nm with a SPEX Fluorolog 1680 0.22 m monochromator and a PMT detector (slit conditions 1/1/1/1 mm, scan speed 2 nm/sec.

Figure 2:
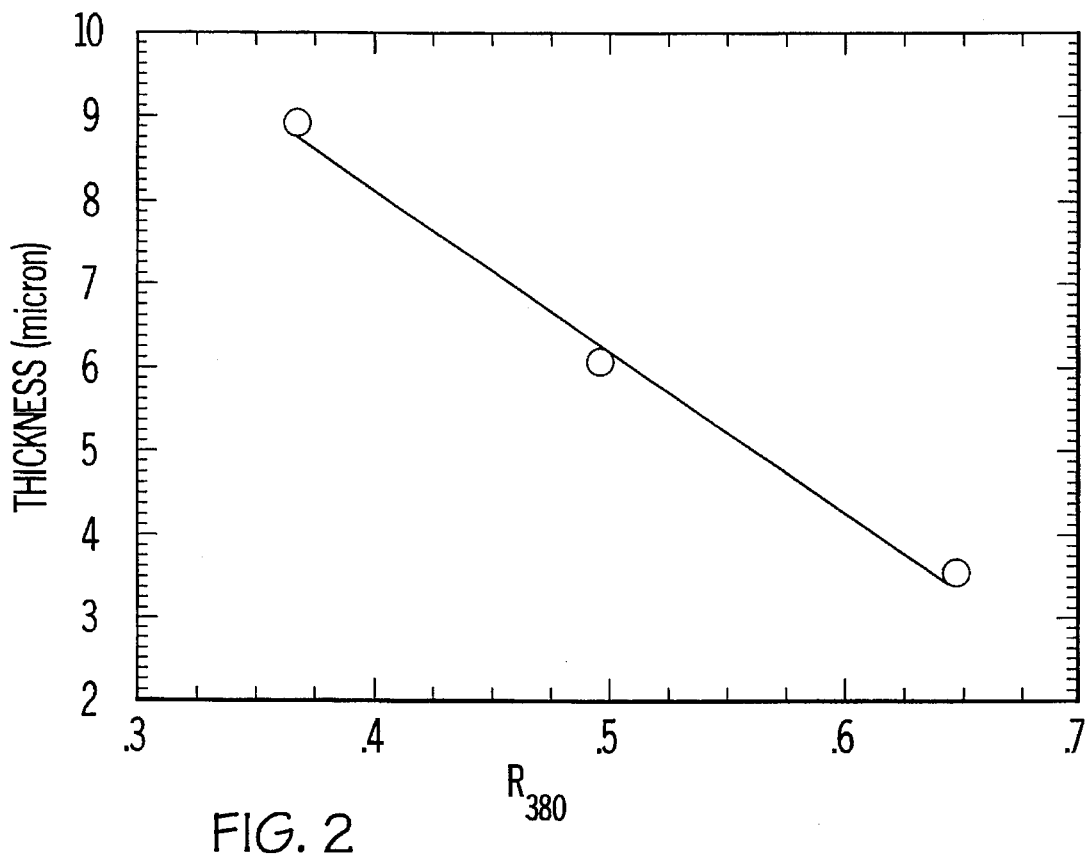
FIG. 2 illustrates a calibration curve for determining the thickness of a silicone acrylate coating on a flat polyethylene terephthalate surface.
Figure 7:
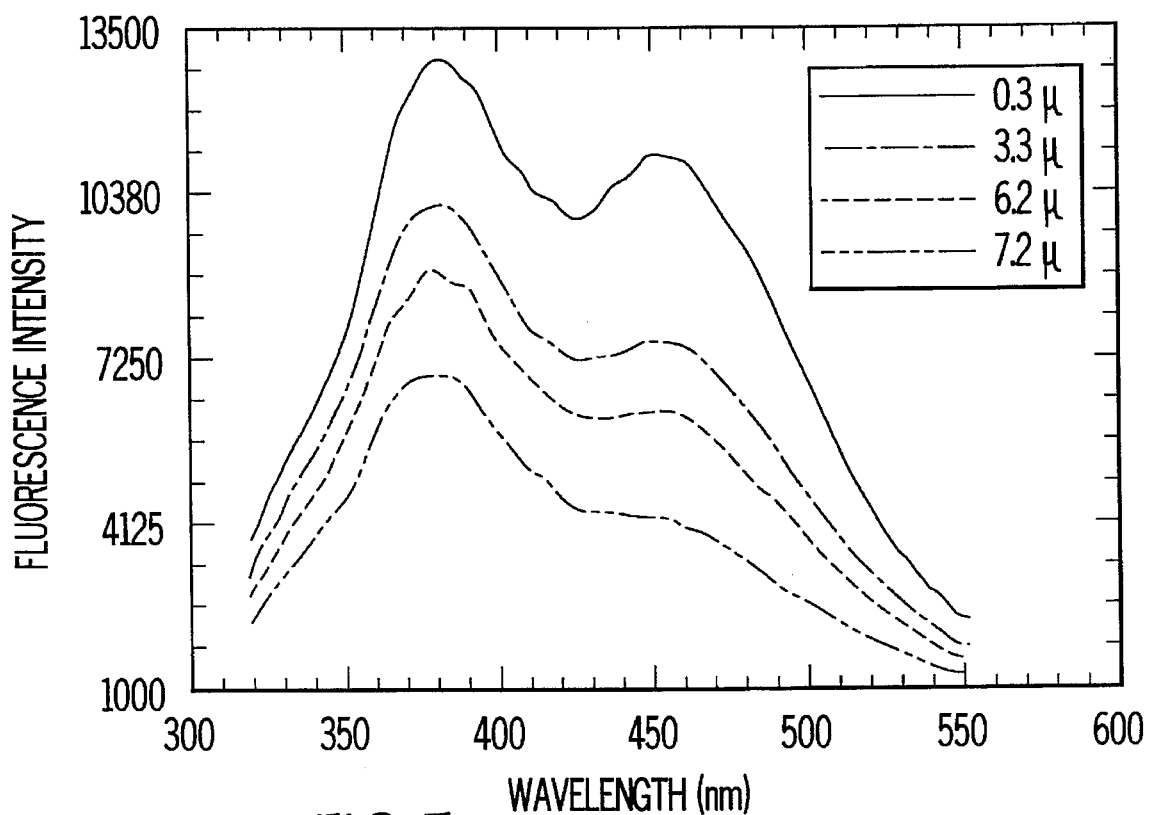
FIG. 7 illustrates the effect of coating thickness on the nascent fluorescence of a PET substrate.

Ratios of intensity of the nascent fluorescence emission through the cured coated to the intensity of the nascent fluorescence emission of the uncoated substrate, were calculated and these ratios, when plotted versus the previously determined thickness of the respective coating on an x,y coordinate graph, provides a linear calibration curve as illustrated in FIG. 2 from which coatings of unknown thickness on a flat substrate can be determined. The effect of coating thickness on the spectrum of nascent PET emission is shown in FIG. 7.

Example 2

Figure 3:
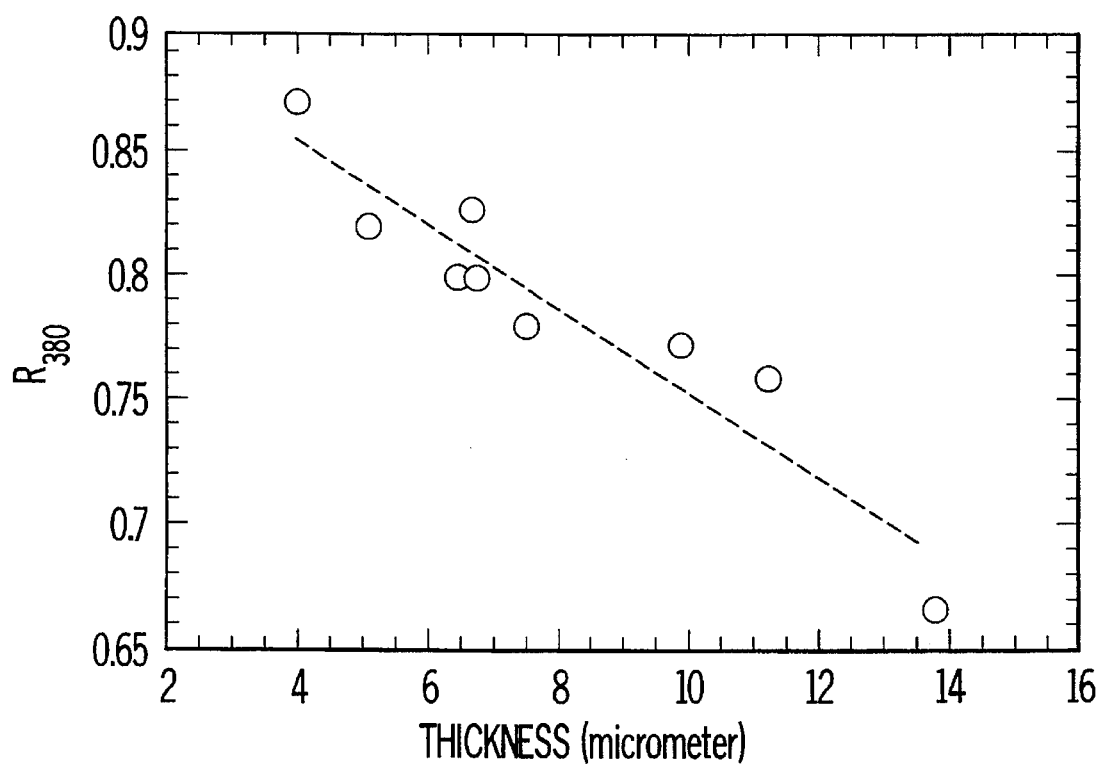
FIG. 3 illustrates a calibration curve for determining the thickness of a silicon acrylate coating on the shoulder of a PET bottle.

The procedure of Example 1 was repeated except that the samples tested were taken from the shoulder section of nine polyethylene terephthalate soda bottles coated with silicone acrylate and cured. The coatings contained 0.16% 1(N,N-dimethylamino)-5-n-butylsulfonamide naphthalene (1,5-DASB) as a fluorescence probe. The coatings were of various thicknesses and were previously determined by independent means. A graph of the nine samples is shown in FIG. 3.

Example 3

Figure 4:
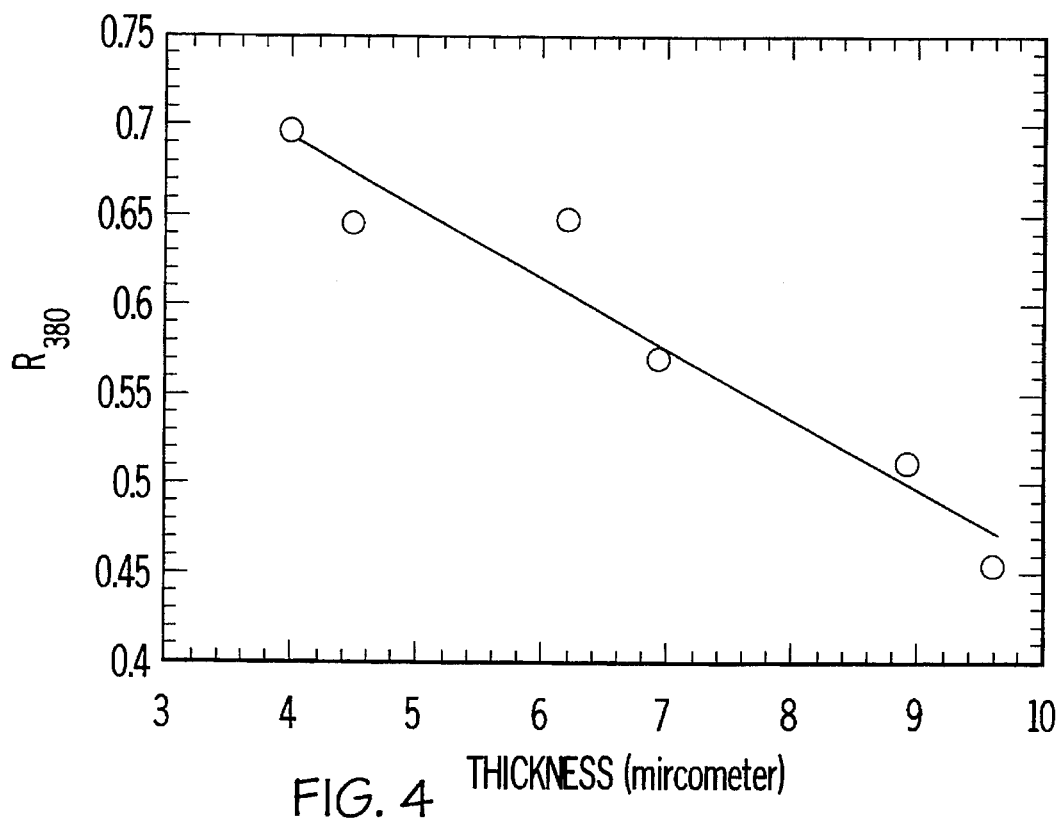
FIG. 4 illustrates a calibration curve for determining the thickness of a silicone acrylate coating on the side wall of a PET bottle.

The procedure of Example 2 was repeated except that the samples were taken from side wall sections of six bottles. A graph of the six samples is shown in FIG. 4.

Example 4

Secondary Optical Fiber Coating; 1,5-DASB probe was doped into the monomer solution (fiber optic secondary coating) at a concentration of =0.016 wt/%. A few drops of that monomer solution was squeezed into two NaCl plates with a 15μ thick TEFLON (polytetrafluoroethylene) spacer at the edges to specifically control the thickness of the film. The fluorescence emission spectrum of the probe was acquired of samples cured for different periods of time with a medium pressure Hg arc lamp. The double bond conversion was measured using a Mattson Galaxy 6020 infrared spectrometer and quantitated according to the disappearance of absorbance at 810 cm$^{-1}$. The results obtained are demonstrated in Table 1 which shows the linear correlation y=1.38+2.63 x) between the C=C conversion and the fluorescence ratio, $I_{470}/I_{560}$. The latter was measured with a Spex Model 2 Fluorimeter using an excitation wavelength of 380 nm with slits of 0.2/0.2/1/1 mm.

TABLE 1

| C = C Conversion | Intensity Ratio |
|---|---|
| 0.00 | 1.32 |
| 0.14 | 1.80 |
| 0.44 | 2.55 |
| 0.49 | 2.75 |
| 0.53 | 2.74 |
| 0.56 | 2.80 |
| 0.58 | 2.85 |

Example 5

Primary Optical Fiber Coating; 1,5-DASB probe was doped into the monomer solution (fiber optic primary coating) at a concentration of =0.016 wt/%. A few drops of that monomer solution was squeezed into two NaCl plates with a 15μ thick TEFLON spacer at the edges to specifically control the thickness of the film. The fluorescence emission spectrum of the probe was acquired of samples cured for different periods of time with a medium pressure Hg arc lamp. The double bond conversion was measured using a Mattson Galaxy 6020 infrared spectrometer and quantitated according to the disappearance of absorbance at 810 cm$^{-1}$. The results obtained are demonstrated in Table 2 which shows the linear correlation (y=1.63+2.32 x) between the C=C conversion and the fluorescence ratio, $I_{470}/I_{560}$. The latter was measured with a Spex Fluorolog Model 2 Fluorimeter using an excitation wavelength of 380 nm with slits of 0.2/0.2/1/1 mm.

TABLE 2

| C = C Conversion | Intensity Ratio |
|---|---|
| 0.00 | 1.65 |
| 0.40 | 2.55 |
| 0.88 | 3.70 |
| 0.96 | 3.85 |

Example 6

A solution of trimethylolpropane triacrylate (TMPTA), dipentaerythritol hydroxy pentacrylate (DPHPA), polyethylene glycol acrylate (PEGA) (40:40:20) was made homogeneous in a sonicator. 2,4-Diiodo-6-butoxy fluorone (DIBF) (5×10$^{-4}$M) and N-phenyl glycine (NPG) (5×10$^{-2}$M) was dissolved in the monomer by sonication. 1,5-DASB probe was doped into the monomer solution at a concentration of ~0.016 wt/%. The sample was irradiated as in example 4) and 5). The double bond conversion was measured using a Mattson Galaxy 6020 infrared spectrometer and quantitated according to the disappearance of absorbance at 810 cm$^{-1}$. The results obtained are demonstrated in Table 3 which shows the linear correlation (y=1.12+3.39 x) between the C=C conversion and the fluorescence ratio, $I_{470}/I_{560}$. The latter was measured with a Spex Fluorolog Model 2 using an excitation wavelength of 380 nm with slits of 0.2/0.2/1/1 mm.

TABLE 3

| C = C Conversion | Intensity Ratio |
|---|---|
| 0.00 | 1.10 |
| 0.175 | 1.70 |
| 0.225 | 1.90 |
| 0.26 | 2.00 |
| 0.275 | 2.07 |
| 0.30 | 2.15 |
| 0.325 | 2.20 |
| 0.34 | 2.25 |

Example 7

Primary Optical fiber Coating; PRODAN probe was doped into the monomer solution (fiber optic primary coating) at a concentration of 5×10$^{-4}$M. A few drops of that monomer solution was squeezed into two NaCl plates with a 15μ thick TEFLON spacer at the edges to specifically control the thickness of the film. The fluorescence emission spectrum of the probe was acquired of samples cured for different periods of time with a medium pressure Hg arc lamp. The double bond conversion was measured using a Mattson Galaxy 6020 infrared spectrometer and quantitated according to the disappearance of absorbance at 810 cm$^{-1}$. The results obtained are demonstrated in Table 4 which shows the linear correlation (y=1.18+2.89 x) between the % C=C conversion and the fluorescence ratio, $I_{470}/I_{560}$. The latter was measured with a Spex Fluorolog Model 2 Fluorimeter using an excitation wavelength of 380 nm with slits of 0.2/0.2/1/1 mm.

TABLE 4

| C = C Conversion | Intensity Ratio |
| --- | --- |
| 0.00 | 1.20 |
| 0.36 | 2.00 |
| 0.525 | 2.70 |
| 0.75 | 3.40 |
| 0.925 | 3.85 |

Example 8

PET Coating; 1,5-DASB probe was doped into the monomer solution (silicone acrylate coating from GE) containing an UV initiator at a concentration of ~0.016 wt/%. A few drops of that monomer solution was squeezed into two NaCl plates with a 15μ thick TEFLON spacer at the edges to specifically control the thickness of the film. The fluorescence emission spectrum of the probe was acquired of samples cured for different periods of time with a medium pressure Hg arc lamp. The double bond conversion was measured using a Mattson Galaxy 6020 infrared spectrometer and quantitated according to the disappearance of absorbance at 810 cm$^{-1}$. The results obtained are demonstrated in FIG. 5 which shows the fluorescence emission spectra for 1,5-DASB in the uncured and the 95% cured composition, and in Table 5 which shows the linear correlation (y=1.34+4.82 x) between the % C=C conversion and the fluorescence ratio, $I_{470}/I_{560}$. The latter was measured with a Spex Fluorolog Model 2 Fluorimeter using an excitation wavelength of 380 nm with slits of 0.2/0.2/1/1 mm.

TABLE 5

| C = C Conversion | Intensity Ratio |
| --- | --- |
| 0.00 | 1.40 |
| 0.16 | 2.10 |
| 0.40 | 3.10 |
| 0.50 | 3.85 |
| 0.55 | 3.90 |
| 0.60 | 4.20 |
| 0.66 | 4.85 |
| 0.69 | 4.65 |

Example 9

PET Coating on Bottles: The degree of polymerization was measured on a GE silicone acrylate coating on a PET bottle as prepared at Pepsi Cola International. The same procedure as used to measure the thickness (Example 2) using an excitation wavelength of 302 nm was employed. The scanning speed of the fluorimeter was at a 90 nm step speed.

Example 10

Polyester Acrylate; 1,5-DASB probe was doped into the monomer solution (polyester acrylate coating containing a UV initiator) at a concentration of ~0.016 wt/%. A few drops of that monomer solution was squeezed into two NaCl plates with a 15μ thick TEFLON spacer at the edges to specifically control the thickness of the film. The fluorescence emission spectrum of the probe was acquired of samples cured for different periods of time with a medium pressure Hg arc lamp. The double bond conversion was measured using a Mattson Galaxy 6020 infrared spectrometer and quantitated according to the disappearance of absorbance at 810 cm$^{-1}$. The results obtained are demonstrated in FIG. 6 and in Table 6 which shows the linear correlation between the % C=C conversion and the fluorescence ratio, $I_{470}/I_{560}$. The latter was measured with a Spex Fluorolog Model 2 Fluorimeter using an excitation wavelength of 380 nm with slits of 0.2/0.2/1/1 mm.

TABLE 6

| C = C Conversion | Intensity Ratio |
| --- | --- |
| 0.00 | 1.30 |
| 0.075 | 1.40 |
| 0.10 | 1.65 |
| 0.20 | 1.95 |
| 0.30 | 2.20 |
| 0.40 | 2.40 |
| 0.50 | 2.60 |
| 0.55 | 2.55 |
| 0.65 | 2.75 |
| 0.70 | 3.10 |
| 0.75 | 3.15 |
| 0.85 | 3.25 |
| 0.90 | 3.15 |

Example 11

E606-6 Unsaturated Polyester Coating: DIBF (0.1% wt), OPPI and diisopropyl dimethylaniline (DIDMA) (molar ratio of 1/2/3) was dissolved in the monomer by sonication. 1,5-DASB probe was doped into the monomer solution at a concentration of ~0.016 wt/%. The sample was irradiated with a 75 w dental lamp. The extent of conversion was measured using a Perkin Elmer DSC-4 thermal analyzer. The results obtained are demonstrated in Table 7 which shows the linear correlation between the extent of conversion and the fluorescence ratio, $I_{470}/I_{560}$.

TABLE 7

| C = C Conversion | Intensity Ratio |
| --- | --- |
| 0.00 | 0.12 |
| 0.60 | 1.70 |
| 0.76 | 2.20 |

Example 12

Figure 6:
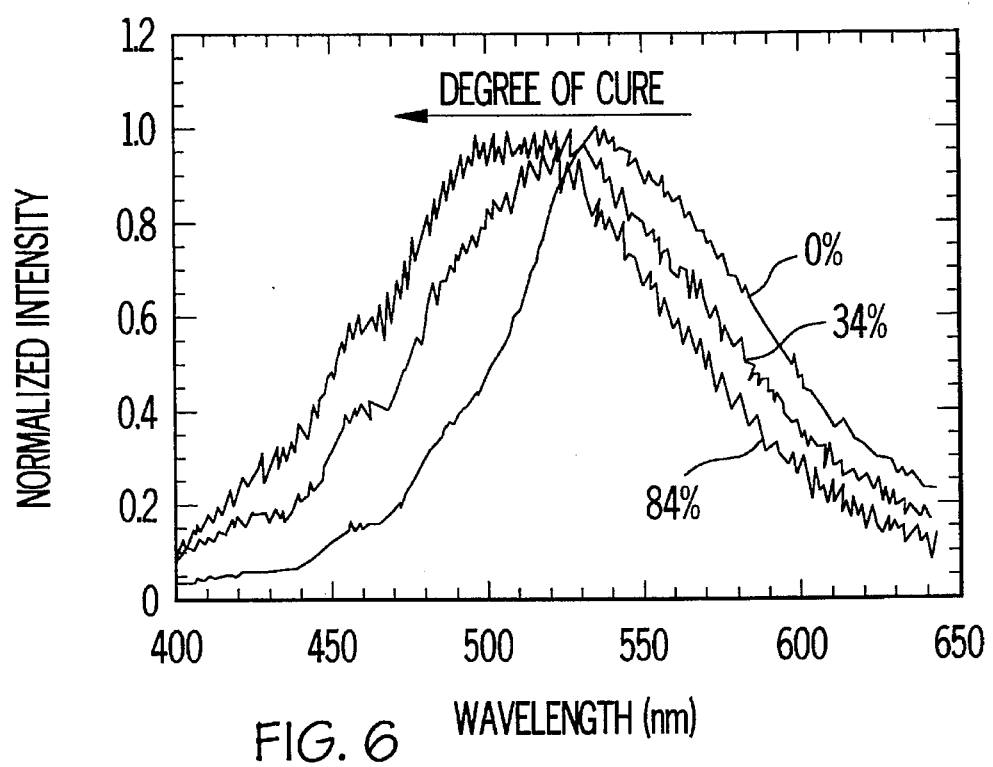
FIG. 6 illustrates a shift in the emission spectrum of 1,5-DASB in a polyester acrylate mixture as a function of degree of cure.

Measurements on the polyester acrylate resin with the ORIEL Spectrograph with a Charge Coupled Device (CCD) detector. DIBF (0.1% wt), octyloxyphenyl phenyliodonium-hexafluoroantimonate (OPPI) and DIDMA (molar ratio of 1/2/3) was dissolved in the monomer (Armstrong Duracoat 4) by sonication. 1,5-DASB probe was doped into the monomer solution at a concentration of ~0.016 wt/%. A few drops of that monomer solution was squeezed into two NaCl plates with a 15μ thick TEFLON spacer at the edges to specifically control the thickness of the film. The fluorescence emission spectrum of the probe was acquired of samples cured for different periods of time with a medium pressure Hg arc lamp. The double bond conversion was measured using a Mattson Galaxy 6020 infrared spectrometer and quantitated according to the disappearance of absorbance at 810 cm$^{-1}$. The results obtained are demonstrated in Table 8 which shows the linear correlation (g=−0.224+0.37 x) between the C=C conversion and the fluorescence ratio, $I_{470}/I_{560}$. The latter was measured with an Oriel Spectrograph with a CCD detector with a measurement time of 2.5 msec. The spectra for three different conversions are shown in FIG. 6. A linear correlation curve between the emission peak position and the extent of double bond conversion was also observed. Therefore, emission peak position can also be used to monitor the degree of cure.

TABLE 8

| C = C Conversion | Intensity Ratio |
|---|---|
| 0 | 0.5 |
| 0.33 | 1.55 |
| 0.85 | 2.90 |

Example 13

Two wavelengths, 432 nmn and 505 nm, were selected which represent the maximum fluorescence emission of a substrate and the probe DASD respectively. The fluorescence intensity ($R=I_{432}/I_{505}$) for several of known thickness samples was obtained experimentally. Each value was an average of 15 measurements which were taken at various positions on a coated substrate of a specified coating thickness. The parameters in the foregoing equation can be obtained from a calibration procedure. Three samples are chosen at random and the A, B, and C values were calculated as:

$A=2.06$ $B=-0.608$ $C=-0.1712$

The foregoing Eq. 1 was rearranged as follows:

$$L = 1/B \times 1 + \left( \frac{C - AB}{B*R - C} \right) \quad \text{Eq. 2}$$

L vs. (1/(B*R–C) was plotted with above values of B and C to give a straight line. The data points on the line represent the average of all the data points. Three data points were taken from the line to obtain a new set of parameters as follows:

| A | = | 1.958 |
|---|---|---|
| B | = | −0.5240 |
| C | = | −0.1496 |

The procedure was repeated using the new parameters to get more accurate values as follows:

$A=2.066$ $B=-0.8209$ $C=-0.444$

With the values determined, the thickness of the coating can be determined using Eq. 1 based on known parameters.

Example 14

It has been demonstrated that a fluorescence probe which is doped into the resin before cure can be used to monitor polymerization processes. The correlation between fluorescence intensity ratio and degree of cure is linear. Therefore, degree of cure can be monitored or determined by examining the fluorescence intensity ratio. Furthermore, the degree of cure of a polymer can also be determined by examining the fluorescence intensity ratio of a probe which is migrated into the polymer network as shown here.

Three fiber optic coating samples were supplied. The outer layer coatings of the samples range in degree of cure from 70 to 90% as measured with a reflective FTIR. The fiber optic was cut into 30 cm lengths. The middle section of the fiber optic was soaked in a solution of acetone containing $6.0 \times 10^{-4}$M DASD (5-N',N-dimethylaminoaphthalene-1-sulfonyl) probe. After the fiber optic was removed from the solution, it was rinsed with pure acetone immediately to remove the probe on the coating surface. Then the fiber was exposure to air so that the solvent inside the coating evaporated. The fluorescence emission spectra of the solvent-free sample were measured by exciting at 380 nm.

Figure 8:
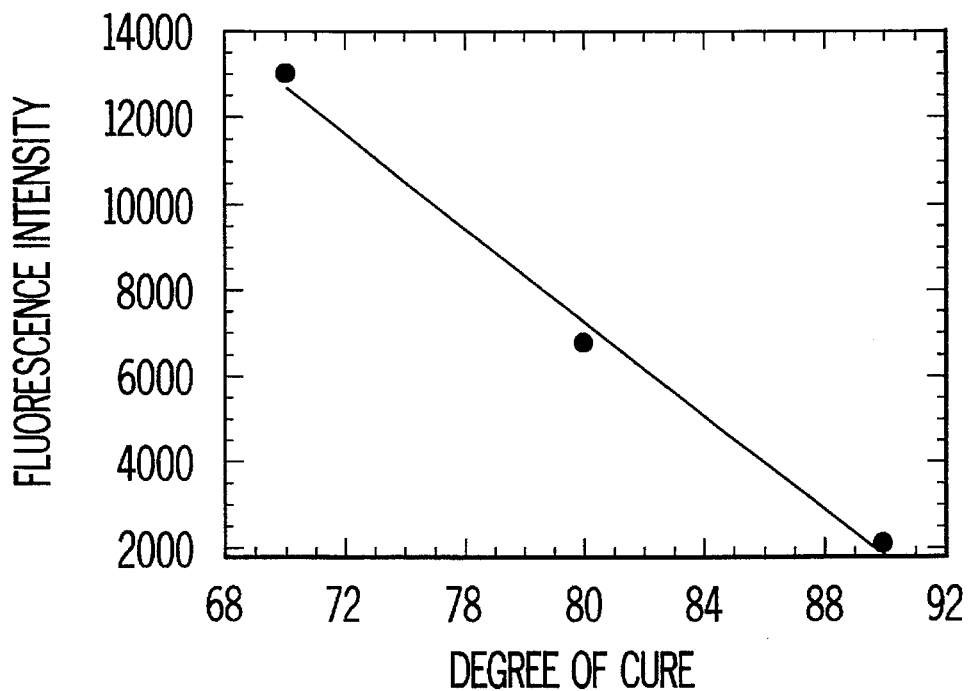
FIG. 8 and FIG. 9 are calibration curves for determining the degree of cure of a polymeric film using post cure diffusion of the probe for a short (FIG. 8) and long (FIG. 9) soaking time.

The higher the degree of cure of a coating, the more difficult it is for a probe to migrate into the coating. The fluorescence emission intensity is proportional to the amount of probe migrated into the coating. During the soaking process, the probe will migrate faster into a sample with a low degree of cure. The fluorescence intensity is inversely proportional to the degree of cure. The soaking time is limited to avoid saturating the coating with the probe. The experiment results indicate that a low intensity is observed for a high cured sample and a high intensity is observed for a low cured sample. FIG. 8 shows the correlation between fluorescence intensity and degree of cure for the fiber optic samples which were soaked in the probe solution for 10 minutes. Once the correlation is established, the degree of cure can be obtained by examining the fluorescence intensity.

Figure 9:
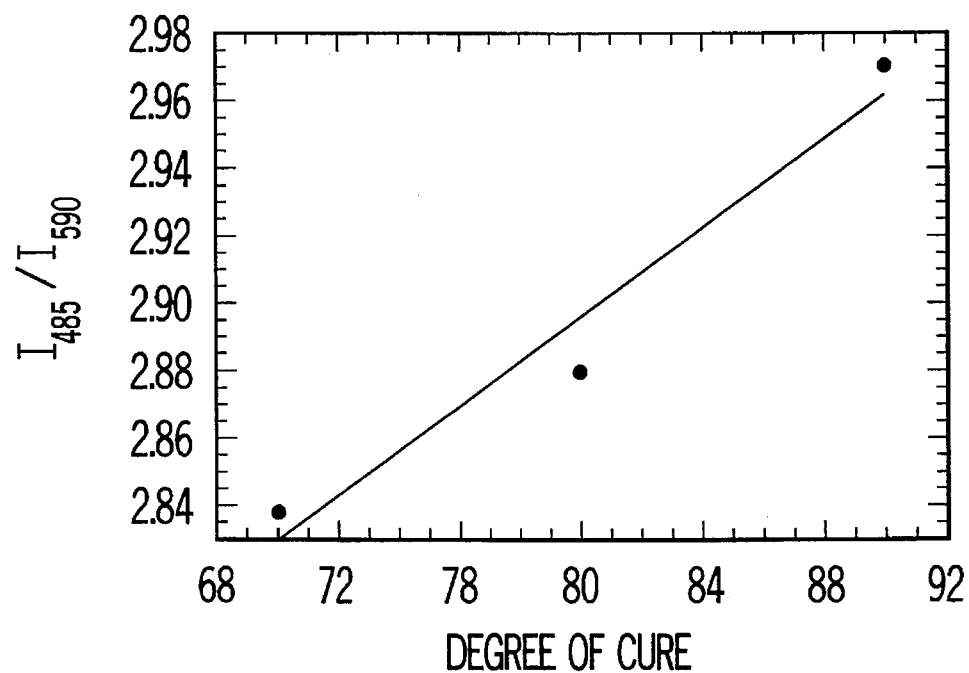

A correlation between fluorescence intensity ratio and degree of cure was also observed in the case that the fiber optic samples soaked for a relatively long period of time, e.g., 1 hour or longer. Since the fluorescence intensity ratio reflects the extent of twisting of the probe in the polymer network, the higher degree of cure, the larger the intensity ratio value. However, in the soaking process the probe molecules will occupy the larger size pores in the polymer network first and then occupy the smaller size pores. If the soaking time is too short, most probe molecules only occupy the larger pores. With an increase in the soaking time the probe molecules migrate further into the polymer network. Finally, the network of the samples is saturated by the probe molecules. In this case the correlation between fluorescence intensity ratio and degree of cure could still be observed. FIG. 9 shows the correlation between fluorescence intensity ratio and degree of cure for the fiber optic samples which were soaked into the probe solution for 1 hour. It is clear that the correlation is linear. Therefore, the degree of cure can be obtained by examining the fluorescence intensity ratio.

Having described the invention in detail with the preferred embodiments illustrated by the examples and elsewhere herein, it will be apparent that modifications and variations are possible without departing from the scope of the invention defined in the appended claims.

What is claimed is:

1. A method for monitoring a property of a polymeric mass comprising the steps of:

adding a fluorescence probe compound capable of fluorescing to a polymeric composition which has the ability to undergo changes in microviscosity, the ratio of the intensity of the fluorescence emission of said compound at two wavelengths changing in response to said changes in said microviscosity of said composition;

curing said composition;

causing said compound to fluoresce;

measuring the fluorescence of said compound;

calculating the ratio of the intensities of fluorescence emission of said compound at two or more wavelengths;

relating said ratio to the monitored property of said composition, the monitored property not being double bond conversion.

2. The method of claim 1 wherein said method is used to monitor a property selected from the group consisting of degree of cure, hardness, abrasion resistance, resistance to stain, tacticity, elasticity, molecular orientation, tensile strength, modulus, the stress state of a solid, wetness and dryness.

3. The method of claim 2 wherein said polymeric mass is a film or coating and said fluorescence is caused by irradiating said coating with actinic radiation.

4. The method of claim 3 wherein said coating is a crosslinkable or polymerizable composition fluorescence probe.

5. The method of claim 4 wherein said fluorescence probe is characterized in that the emission spectrum of said probe exhibits a multiplicity of emissions with a large Stokes shift, and said emissions exhibit both a wavelength change and an intensity change upon curing said composition.

6. The method of claim 4 wherein said probe exhibits a first set of excited state equilibrium conformations in said composition prior to curing and a second set of excited state equilibrium conformations in said composition after curing, and said first and second conformations exhibit distinctly different emission spectra.

7. The method of claim 6 wherein said probe exhibits multiple fluorescence emissions resulting from twisted intramolecular charge transfer in said probe.

8. The method of claim 4 wherein said probe is selected from the group consisting of dansylamide, 1-(N,N-dimethylamino)-5-n-butylsulfonamido-naphthalene (1,5-DASB), 2-(N,N-dimethylamino)-5-n-butyl-sulfonamide-naphthalene (2,5-DASB), N-N-dimethylamino-5-propionylnaphthalene, 4-(N-N-dimethylamino) benzonitrile, ethyl 4-(N,N-dimethylamino benzoate, 2-([4-(N,N-dimethylamino) benzoyl]oxy) ethyl methacrylate, butyl 4-(N-pipridino) benzoate, butyl 4-(N-morpholino) benzoate, butyl 4-(N,N-dimethylamino) benzoate, n-butyl 2-dimethylamino-5-naphthalene sulfonate, N-(4'-cyanophenyl)-carbazole, N-(4'-butyl benzoate)-carbazole, N-(1'-naphthyl)-carbazole and 9, 9'-dianthryl.

9. The method of claim 8 wherein said fluorescence probe is 1,5-DASB.

10. The method of claim 3 wherein said coating includes a curable acrylate selected from the group consisting of silicon acrylates, urethane acrylates, epoxy acrylates, polyester acrylates and unsaturated polyesters.

11. The method of claim 3 wherein said coating includes a vinyl compound selected from the group consisting of styrene, vinyl chloride, and vinyl ethers.

12. The method of claim 3 wherein said coating includes an epoxide.

13. The method of claim 1 wherein the step of relating includes comparing said ratio to calibration data in which said monitored property is independently determined as a function of said ratio.

14. The method of claim 1 wherein one of said two or more wavelengths is about 200 nm to 400 nm.

15. The method of claim 14 wherein said one of said two or more wavelengths is 302 nm.

* * * * *